United States Patent

Miki

[11] Patent Number: 5,547,993
[45] Date of Patent: Aug. 20, 1996

[54] THERAPEUTIC AGENT FOR GLAUCOMA

[75] Inventor: Hirohiko Miki, Osaka-fu, Japan

[73] Assignee: Mitsubishi Chemical Corporation, Tokyo, Japan

[21] Appl. No.: 547,541

[22] Filed: Oct. 24, 1995

[51] Int. Cl.$^6$ .................................................. A61K 31/135
[52] U.S. Cl. ........................................... 514/648; 514/913
[58] Field of Search ...................... 514/648, 913

[56] References Cited

U.S. PATENT DOCUMENTS

| | | | |
|---|---|---|---|
| 4,091,114 | 5/1976 | Kikumoto et al. | 514/648 |
| 4,507,322 | 3/1985 | Kuriyama et al. | 514/648 |
| 4,576,966 | 3/1986 | Kuriyama et al. | 514/648 |

*Primary Examiner*—Raymond Henley, III
*Attorney, Agent, or Firm*—Wenderoth, Lind & Ponack

[57] ABSTRACT

The present invention provides a novel drug for treating glaucoma. The present invention relates to a therapeutic agent for glaucoma which comprises an aminoalkoxybibenzyl represented by the formula (I):

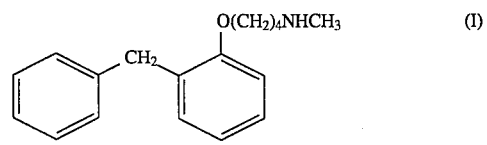

or a hydrate or pharmaceutically acceptable salt thereof as an active ingredient.

12 Claims, No Drawings

THERAPEUTIC AGENT FOR GLAUCOMA

FIELD OF THE INVENTION

The present invention relates to a therapeutic agent for glaucoma.

BACKGROUND OF THE INVENTION

Glaucoma is considered to be a group of diseases wherein the entoptic tissue (particularly function of optic nerve cell) is damaged from lesions causing an abnormal ocular tension. Normally, the principal factors of the mechanism causing lesions are considered to be ischemic symptoms and disorder of optic nerve axonal flow due to mechanical compression in the lamina cribrosa caused by an increase in ocular tension. However, the mechanism of the increase in ocular tension is not clear at present.

For the treatment of the disease, glaucoma, a drug or surgical therapy has been mainly performed aiming at returning the increased ocular tension to a normal level. There are few treatments for protecting an optical nerve function directly. For instance, a vitamin B12 formulation can be used as a nutrient agent for protecting the optical nerve, and a calcium antagonist or an enzyme formulation can be used for the purpose of improving blood flow in the optic disc to protect the optical nerve cells. However, effectiveness of these agents on the disorder of the visual field caused by glaucoma is not clear. Besides, there is a problem that side effects can occur during a long-term usage thereof.

Therefore, the purpose of the present invention is to provide a therapeutic agent enabling an effective drug therapy for glaucoma. Further purpose of the present invention is to provide a therapeutic agent for glaucoma which has reduced side effects related to a long-term usage thereof.

SUMMARY OF THE INVENTION

In order to solve the above problems, the present inventors have studied intensively. As a result, it has been found that 2-(4-methylaminobutoxy) diphenylmethane or a hydrate or pharmaceutically acceptable salt thereof is useful for treating glaucoma, and the present invention has been accomplished.

The present inventors have found that 2-(4-methylaminobutoxy)diphenylmethane, which is disclosed in Japanese Patent Publication (Kokoku) No. Hei 60-6349 specification, is useful for treating infantile hyperkinetic disorders. The present invention has been established based on such finding.

It is reported in GB 1512880 publication that 2-(4-methylaminobutoxy)diphenylmethane possesses an antidepressant activity, and it is also known from EP 103897 publication that this compound is useful as an agent for improving and treating pathergasia caused by intracranial organic disease such as cerebral hemorrhage or the like. A medicine containing 2-(4-methylaminobutoxy) diphenylmethane hydrochloride as an effective ingredient, which has a generic name of "bifemelane hydrochloride", is commercially available and has been used for improving cerebral nerve function, in particular, for treating aftereffect of cerebral occlusion or hemorrhage accompanied by volition lowering and emotional disorder.

According to the present invention, a therapeutic agent for glaucoma, which contains as an essential component 2-(4-methylaminobutoxy) diphenylmethane of the formula (I):

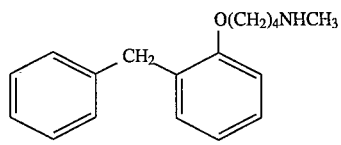

or a hydrate or pharmaceutically acceptable salt thereof, is provided.

The compound of the formula (I) can be easily prepared according to the method as described, for example, in Japanese Patent Publication Kokoku) No. Sho 60-6349 specification (Example 1) or Japanese Patent Publication (Kokoku) No. Hei 2-33689 (Column 4 -5). A free form of said compound, its hydrate or a physiologically acceptable acid addition salt thereof may be used as an active ingredient of the pharmaceutical. composition of the present invention.

The pharmacologically acceptable acid addition salts include mineral acid salts such as hydrochloride, hydrobromide, hydroiodide, suifate, nitrate and phosphate; or organic acid salts such as acetate, maleate, fumarate, citrate, oxalate, succinate, tartarate, malate, mandelate, methanesulfonate, p-toluenesulfonate and 10-camphor sulfonate, with the hydrochloride of said compound being preferred, which is commercially available as a substance having generic name "bifemetane hydrochloride".

Route of administration of the therapeutic agent is not particularly limited, and it may be administered by oral and parenteral routes, with oral used alone for treating said disorder, but ordinarily, a conventional pharmaceutical formulation comprising the compound of the formula (I) together with pharmacologically and pharmaceutically acceptable additives may be prepared. The pharmacologically and pharmaceutically acceptable additives include, for example, excipients, disintegrators or disintegration aids, binders, lubricants, coating agents, pigments, diluents, bases, dissolving agents or solubilizers, isotonic agents, pH regulators, stabilizers, propellants, adhesives, and the like.

Appropriate formulations for oral administration include, for example, tablets, capsules, powders, fine granules, granules, solutions, syrups and the like. Appropriate formulations for parenteral administration include, for example, injections, drops, suppositories, inhalants, plasters, and the like.

The formulations suitable for oral, percutaneous or transmucosai administration may contain pharmaceutically acceptable additives including excipients such as glucose, lactose, D-mannitol, starch or crystalline cellulose; disintegrators or disintegration aids such as carboxymethyl cellulose, starch or calcium carboxymethyl cellulose, etc.; binders such as hydroxypropyl cellulose, hydroxypropyl methyl cellulose, polyvinylpyrrolidone or gelatin; lubricants such as magnesium stearate or talc; coating agents such as hydroxypropyl methyl cellulose, saccharose, polyethylene glycol or titanium oxide; and bases such as vaseline, liquid paraffin, polyethylene glycol, gelatin, kaolin, glycerin, purified water or hard fat. Further, such formulations may be prepared by adding pharmaceutical additives including propellants such as fron, diethyl ether or compressed gas; adhesives such as sodium polyacrylate, polyvinyl alcohol, methyl cellulose, polyisobutylene or polybutene; basic cloth such as cotton cloth or plastic sheet; and the like.

The formulations appropriate for injection or drip infusion may contain pharmaceutical additives including dissolving agents or dissolution aids which can form aqueous injections or those of the dissolving type-in use such as distilled water for injection, physiological brine or propylene glycol; isotonic agents such as glucose, sodium chloride, D-mannitol or glycerin; pH regulators such as inorganic acids, organic acids, inorganic bases or organic bases; and the like.

Since pharmaceutical formulations for treating cerebral nerve function which contain the compound of the formula (I) as an active ingredient are already commercially available under the generic name "bifemelane hydrochloride" and trade names "Alnert" and "Celeport" by Fujisawa Pharmaceutical Chemical Industries, Co., Ltd. and Eisai Co., Ltd., respectively. Said commercially available formulations may be used as a pharmaceutical composition of the present invention for treating hyperkinetic disorders.

Appropriate dosage of said agent is not limitative and can be appropriately determined depending upon administering route, age or body weight of patients, symptoms of the disease, and the like. For example, for oral administration, the daily dosage for adult, which corresponds to about 5–300 mg. preferably about 50–200 mg, particularly preferably 150 mg of the active ingredient can be used as a basis for calculating the daily dosage for infants. The pharmaceutical composition of the present invention may be administered once a day or for several times at devided daily dose, and the period of administration may be appropriately determined, depending upon the age of particular infant and degree of the symptoms. Further, 2-(4-methylaminobutoxy)diphenylmethane incorporated into the composition of the present invention is almost nontoxic as will be noted from the acute toxicity value listed in Table 1 of Japanese Patent Publication (Kokoku) No. Hei 2-33689 specification. Since the pharmaceutical composition aims at applying to infants, it may be easily understood that such characteristics of said composition is very advantageous to this invention.

EXAMPLE

Pharmaceutical formulations of the present invention are shown below, but the formulations of the present invention are not limited to those examples.

| Formulation 1. | |
| --- | --- |
| 2-(4-Methylaminobutoxy)diphenylmethane hydrochloride | 100 g |
| Mannit | 300 g |
| Corn starch | 450 g |
| Lactose | 300 g |
| Hydroxypropyl cellulose | 38 g |
| Calcium stearate | 12 g |

The above ingredients are admixed in a conventional manner to give capsules weighing 120 mg per capsule.

| Formulation 2. | |
| --- | --- |
| 2-(4-Methylaminobutoxy)diphenylmethane hydrochloride | 100 g |
| Corn starch | 200 g |
| Lactose | 500 g |
| Calcium carboxymethyl cellulose | 150 g |
| Polyvinylpyrrolidone | 75 g |
| Talc | 75 g |
| Microcrystalline cellulose | 250 g |

The above ingredients are admixed in a conventional manner and granulated and subjected to a tableting machine to give tablets weighing 120 mg per tablet.

| Formulation 3. | |
| --- | --- |
| 2-(4-Methylaminobutoxy)diphenylmethane hydrochloride | 50 mg |

| Formulation 3. | |
| --- | --- |
| Hydroxypropyl cellulose | 4 mg |
| Hydroxypropylmethyl cellulose | 50 mg |
| Sodium citrate | 50 mg |
| Sodium saccharin | 3 mg |
| Saccharose | optimum dose |
| Corn starch | 29 mg |
| D-Mannitol | 67 mg |
| Glycerin monostearate | 200 mg |
| Eudragit L-30D55 | 71 mg |
| Macrogoal 6000 | 7 mg |
| Talc | 21 mg |
| Sodium laurylsulfate | trace |
| Perfume | trace |
| | 1000 mg |

The above ingredients are admixed in a conventional manner to give dry syrup.

| Formulation 4. | |
| --- | --- |
| 2-(4-Methylaminobutoxy)diphenylmethane hydrochloride | 50 mg |
| Hydroxypropyl cellulose | 70 mg |
| Corn starch | 50 mg |
| D-Mannitol | optimum dose |
| Aminoalkyl methacrylate copolymer E | 85 mg |
| Talc | 60 mg |
| Calcium stearate | 5 mg |
| | 1000 mg |

The above ingredients are admixed to give granules.

Clinical Tests

Case 1

Twenty-five patients with primary open-angle glaucoma, whose ocular tension is kept at 20 mmHg by eye drops and who have a progressive constriction in the visual field, detected by perimetry using Humphrey's Ocular Field Stat Pack II, were orally administered a tablet containing 50 mg of bifemelane hydrochloride for 3 times a day for 24 months, and therapeutic effects thereof on the progressive constriction in the visual field Was examined. The visual field was measured using Humphrey's static quantitative perimeter before and 6, 12, 18 and 24 months after administration of bifemelane hydrochloride. The therapeutic effects on the visual field were determined by comparing mean sensitivities in time-course. As a result, 50% of the patients was judged as "improved" and 12% as "unchanged", when compared with the visual field before administration of bifemelane hydrochloride.

Case 2

In sixteen patients, who have glaucoma with normal ocular tension as well as progressive constriction in the visual field, and who have not received eye drops treatment, therapeutic effects of bifemelane hydrochloride on the changes in the visual field were examined in the same method as described above. As a result, 47% of the patients was judged as improved and 16% as unchanged, when compared with the visual field before administration.

The above results demonstrated that, for glaucoma with progressive constriction in the visual field, bifemelane hydrochloride exhibited therapeutic effects for 62% of the patients having open-angle glaucoma and 63% of the patients who had glaucoma with normal ocular tension.

These results clearly suggest that bifemelane enables an effective new drug therapy for glaucoma, since at present time there are few drugs effective on progressive constriction in the visual field accompanying glaucoma.

What is claimed is:

1. A method of treating glaucoma which comprises administering to a patient in need thereof, an effective amount of a compound represented by the formula (I):

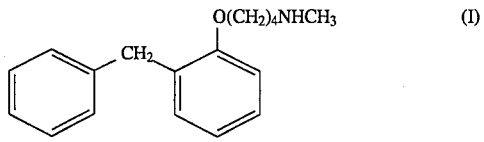

or a hydrate or pharmaceutically acceptable salt thereof.

2. The method according to claim 1, wherein said compound is a pharmaceutically acceptable salt selected from the group consisting of mineral acid salts and organic acid salts.

3. The method according to claim 2, wherein the mineral acid salt is selected from the group consisting of hydrochloride, hydrobromide, hydroiodide, sulfate, nitrate and phosphate.

4. The method according to claim 2, wherein the organic acid salt is selected from the group consisting of acetate, maleate, fumarate, citrate, oxalate, succinate, tartarate, malate, mandelate, methanesulfonate, p-toluenesulfonate and 10-camphor sulfonate.

5. The method according to claim 1, wherein said compound is administered in a pharmaceutical composition comprising the compound and a pharmaceutically acceptable additive.

6. The method according to claim 5, wherein the pharmaceutical composition comprises said compound and at least one pharmaceutically acceptable additive selected from the group consisting of excipients, disintegrators or disintegrating aids, binders, lubricants, coating agents, pigments, diluents, bases, dissolving agents or solubilizers, isotonic agents, pH regulators, stabilizers, propellants and adhesives.

7. The method according to claim 1, wherein said compound is administered orally.

8. The method according to claim 1, wherein said compound is administered parenterally.

9. The method according to claim 1, wherein said compound is administered percutaneously.

10. The method according to claim 1, wherein said compound is administered transmucosally.

11. The method according to claim 1, wherein said compound is administered in a daily dose of 15–300 mg.

12. The method according to claim 1, wherein said compound is administered in a daily dose of 50–200 mg.

* * * * *